US006747132B2

(12) United States Patent
Privalle et al.

(10) Patent No.: US 6,747,132 B2
(45) Date of Patent: Jun. 8, 2004

(54) METHODS FOR THE SYNTHESIS OF A MODIFIED HEMOGLOBIN SOLUTION

(75) Inventors: Christopher Thomas Privalle, Durham, NC (US); Cyrus John Stacey, Raleigh, NC (US); Todd Lewis Talarico, Cary, NC (US)

(73) Assignee: Apex Biosciences, Inc., Research Triangle Park, NC (US)

( * ) Notice: Subject to any disclaimer, the term of this patent is extended or adjusted under 35 U.S.C. 154(b) by 39 days.

(21) Appl. No.: 09/930,905

(22) Filed: Aug. 16, 2001

(65) Prior Publication Data

US 2002/0099175 A1 Jul. 25, 2002

Related U.S. Application Data

(60) Provisional application No. 60/253,758, filed on Nov. 29, 2000.

(51) Int. Cl.[7] ............ A61K 38/42; C07K 1/34; C07K 14/805
(52) U.S. Cl. ............ 530/385; 514/6; 530/427
(58) Field of Search ............ 424/94.2, 94.3, 424/94.4; 514/6; 530/385, 427

(56) References Cited

U.S. PATENT DOCUMENTS

| 4,301,144 A | 11/1981 | Iwashita et al. ............... 514/6 |
| 4,412,989 A | 11/1983 | Iwashita et al. ............ 530/385 |
| 4,529,719 A | 7/1985 | Tye ............... 514/6 |
| 4,670,417 A | 6/1987 | Iwasaki et al. ............... 514/6 |
| 4,826,811 A | 5/1989 | Sehgal et al. .................. 514/6 |
| 5,084,558 A | 1/1992 | Rausch et al. ............... 530/385 |
| 5,194,590 A | 3/1993 | Sehgal et al. ............... 530/385 |

(List continued on next page.)

FOREIGN PATENT DOCUMENTS

| EP | 0 156 961 A2 | 10/1985 |
| WO | WO 90/15613 | 12/1990 |

OTHER PUBLICATIONS

Li, H., et al., "Polynitroxylation Neutralizes the Hypertensive Effect of αα–Crosslinked Hemoglobin without Affecting Nitric Oxide Scavenging," 6th Annual Meeting of the Oxygen Society, Nov. 18–22, 1999, Abstract No. 234.

Mao, G. et al. Superoxide Dismutase (SOD)–Catalase Conjugates, *Journal of Biological Chemistry*, Jan. 1993, pp. 416–420, vol. 268(1), The American Society for Biochemistry and Molecular Biology, Inc. , USA.

Privalle, C., et al., "Pyridoxalated Hemoglobin Polyoxyethylene: A Nitric Oxide Scavenger With Antioxidant Activity For The Treatment Of Nitric Oxide–Induced Shock," *Free Radical Biology and Medicine*, May 2000, pp. 1507–1517, vol. 28(10), USA.

(List continued on next page.)

*Primary Examiner*—Jeffrey E. Russel
(74) *Attorney, Agent, or Firm*—Alston & Bird LLP (57) ABSTRACT

The present invention employs a filtration step during the hemoglobin purification process that substantially decreases viral contamination of a hemoglobin solution. The filtration means can be used to separate hemoglobin and several endogenous antioxidant enzymes from red blood cell stroma and potential adventitious agents. The purified hemoglobin/antioxidant composition is then subjected to a chemical modification process. The resulting modified hemoglobin/antioxidant composition is then fractionated to remove unmodified hemoglobin species and residual reactants, formulated in electrolytes and rendered sterile. The resulting modified hemoglobin product is substantially free of viral contamination and contains at least one endogenous antioxidant enzyme that retains antioxidant activity.

20 Claims, 3 Drawing Sheets

U.S. PATENT DOCUMENTS

| | | | |
|---|---|---|---|
| 5,217,648 A | 6/1993 | Beissinger et al. | 514/6 |
| 5,234,903 A | 8/1993 | Nho et al. | 514/6 |
| 5,264,555 A | 11/1993 | Shorr et al. | 530/385 |
| 5,281,579 A | 1/1994 | Estep | 514/6 |
| 5,296,465 A | 3/1994 | Rausch et al. | 514/6 |
| 5,312,808 A | 5/1994 | Shorr et al. | 514/6 |
| 5,386,014 A | 1/1995 | Nho et al. | 530/385 |
| 5,439,591 A | 8/1995 | Pliura et al. | 530/385 |
| 5,464,814 A | 11/1995 | Sehgal et al. | 514/6 |
| 5,478,805 A | 12/1995 | Shorr et al. | 514/6 |
| 5,545,328 A | 8/1996 | Pliura et al. | 530/385 |
| 5,606,025 A | 2/1997 | D'Agnillo et al. | 530/385 |
| 5,741,894 A | 4/1998 | Azari et al. | 530/385 |
| 5,840,701 A | 11/1998 | Hsia | 514/21 |
| 5,905,141 A | 5/1999 | Rausch et al. | 530/385 |
| 5,998,361 A | 12/1999 | Bucci et al. | 514/2 |

OTHER PUBLICATIONS

Privalle, C., et al., "Pyridoxalated Hemoglobin–Polyoxyethylene(PHP): A Nitric Oxide Scavenger With—Antioxidant Properties," $4^{th}$ Annual Meeting of the Oxygen Society, 1997, USA.

Privalle, C., et al., " Pyridoxalated Hemoglobin Polyoxyethylene (Php)—A Modified Hemoglobin Therapeutic With Sod–Catalase Activity," $6^{th}$ Annual Meeting of the Oxygen Society, Nov. 18–22, 1999, Abstract No. 254.

Quebec, E. and Chang, T., "Superoxide Dismutase and Catalase Cross–Linked to Polyhemoglobin Reduces Methemoglobin Formation In Vitro," Art. Cells. Blood Subs., and Immob. Biotech., 1995, pp. 693–705, vol. 23(6), Marcel Dekker, Inc.

Raznck S., et al., "Crosslinked Hemoglobin–Superoxide Dismutase–Catalase Scavenges Free Radicals in a Rat Model of Intestinal Ischemia–reperfusion Injury," 1997, Art. Cells, Blood Subs. and Immob. Biotech. pp. 181–192, vol. 25(1&2), Marcel Dekker, Inc.

Sato, et al., "Synthesis and Characterization of Superoxide Dismutase–Deferoxamine Conjugate Via Polyoxethylene: A New Molecular Device for Removal of a Variety of Reactive Oxygen Species", Bioconjugate Chem., 1995, pp. 249–254, vol. 6(3), American Chemical Society, USA.

Talarico, T., et al., "Chemical Characterization of Pyridoxalated Hemoglobin Polyoxyethylene Conjugate," BBA, Jan. 2000, pp. 53–65, vol. 1476, Elsevier Science, BV.

Azari, M., et al., "Diaspirin Crosslinked Hemoglobin (DCLHb™): Characterization of the Process and the Product Manufactured under GMP Requirements for Clinical Studies," Art. Cells, Blood Subs., and Immob. Biotech., 1994, pp. 701–708, vol. 22(3).

Bechtel, M., et al., "Virus Removal or Inactivation in Hemoglobin Solutions by Ultrafiltration or Detergent/Solvent Treatment," Biomater. Artif. Cells Artif. Organs, 1988, pp. 123–128, vol. 16(1–3).

Bone, H., et al., "Pyridoxalated Hemoglobin Polyoxyethylene Conjugate Reverses Hyperdynamic Circulation in Septic Sheep," J. Appl Physiol, 1998, pp. 1991–1999, vol. 84, American Physiological Society, USA.

Chang, T., " Future Prospects for Artificial Blood", TIBTECH, Feb. 1999, pp. 61–67, vol. 17(2), Elsevier Trends Journals, UK.

D'Agnillo, F. and Chang, T., "Polyhemoglobin–Superoxide Dismutase–Catalase as a Blood Substitute with Antioxidant Properties," Nature Biotechnology, 1998, pp. 667–671, vol. 16.

D'Agnillo,F. and Chang, T. "Reduction of Hydroxyl Radical Generation in a Rat Hindlimb Model of Ischemia–Reperfusion Injury Using Crosslinked Hemoglobin–Superoxide Dismutase–Catalase," 1997, Art. Cells, blood Subs. and Immob. Biotech., 1997, pp. 163–180, vol. 25, Marcel Dekker, Inc.

D'Agnillo, F. and Chang, T., "Cross–Linked Hemoglobin–Superoxide Dismutase–Catalase Scavenges Oxygen–Derived Free Radicals and Prevents Methemoglobin Formation and Iron Release," 1993, Biomat., Art. Cells. & Immob. Biotech., 1993, pp. 609–621, vol. 21(5), Marcel Dekker, Inc.

D'Agnillo, F. and Chang, T., "Crosslinked Hemoblobin–Superoxide Dismutase–Catalase Reduces Hemoprotein–Associated Free Radical Events in Models of In Vitro and In Vivo Oxidative Stress," Abstracts from the VI International Symposium on Blood Substitutes, 1996, vol. 24(4), p. 327.

Estep, T., et al., "The Purification of Hemoglobin Solutions by Heating," The Red Cell: Seventh Ann Arbor Conference, 1989, pp. 325–338, Alan R. Liss, Inc.

Farmer, M., et al., "Validation of Vinus Inactivation by Heat Treatment in the Manufacture of Diaspirin Crosslinked Hemoglobin," 1992, Biomater. Artif. Cells Immobilization Biotechnol., pp. 429–433, vol. 20.

Highsmith, F., et al., "An Improved Process for the Production of Sterile Modified Haemoglobin Solutions," Biologicals, 1997, pp. 1–12, vol. 25, The International Association of Biological Standardization, USA.

Iwashita, Y., "Hemoglobin Conjugated with Polyoxyethylene", Artificial Red Cells, 1995, pp. 151–176, John Wiley and Sons Ltd.

Chartrand, S., " A Recombination Hemoglobin to Counter the Septic Shock Brought on by Postoperative Infection," New York Times, Apr. 25, 1994, p. C2.

"Oxygen Therapeutics: Hemoglobin's New Role—Development Opportunities," Drug & Market Development, Jul. 2, 1996, vol. 7(7), pp. 164–167.

Privalle, C. et al., "Pyridoxalated Hemoglobin Polyoxyethylene (PHP): A Hemoglobin–Based Nitric Oxide Scavenger with Antioxidant Properties," Nitric Oxide, 1998, vol. 2(2), p. 79.

Privalle, C. et al., "Pyridoxalated Hemoglobin Polyoxyethylene (PHP): Nitric Oxide Scavenging and Antioxidant Properties," Free Radical Biology & Medicine, 1998, val. 25(1), p. 565, Abstract No. 178.

PPHb=Pyridoxalated Polyoxyethylene Hemoglobin
PHP=Pyridoxalated Hemoglobin Polyoxyethylene (Final Product)

METHODS FOR THE SYNTHESIS OF A MODIFIED HEMOGLOBIN SOLUTION

CROSS-REFERENCE TO RELATED APPLICATIONS

This application claims the benefit or U.S. Provisional Application No. 60/253,758, filed Nov. 29, 2000, which is hereby incorporated herein in its entirety by reference.

FIELD OF THE INVENTION

The invention relates to a method of preparing a chemically modified hemoglobin solution.

BACKGROUND OF THE INVENTION

Advances have occurred in recent years in the development of hemoglobin-based blood substitutes. Such transfusional fluids serve as alternatives to whole blood or blood fractions for use as oxygen carriers, plasma expanders, enhancers of radiation and chemotherapy, and scavengers of nitric oxide. Hemoglobin-based blood substitutes are produced by modification of ultra-purified or stroma free hemoglobin using a variety of intermolecular or intramolecular reactions. These various modifications are designed to stabilize the protein, modulate oxygen-binding properties to acceptable physiological levels, and to decrease renal toxicity. Due to the presence of the heme and iron moieties, the hemoglobin molecule has potential toxicity resulting from rapid autooxidation of hemoglobin following free radical interactions and hemoglobin-mediated vasoconstriction. Further, hemoglobin can react with cellular oxidants such as hydrogen peroxide, resulting in the production of both methemoglobin ($Fe^{3+}$) and ferrylhemoglobin ($Fe^{4+}$), a strong oxidant reported to cross-link proteins and peroxidize lipids.

Antioxidant systems within the red blood cells control these free radical reactions and protect the function and structural integrity of hemoglobin. For instance, in the red blood cell, endogenous antioxidant enzymes, such as superoxide dismutase (SOD) and catalase (CAT), catalyze the breakdown of superoxide and hydrogen peroxide ($H_2O_2$), respectively, and hence serve to maintain the functional and structural integrity of hemoglobin. Hence, the oxygen delivery capability of polymerized hemoglobin solutions may be enhanced through the association of these antioxidant enzymes.

One recent experimental approach has resulted in the design of a second generation hemoglobin based oxygen carrier in which the free radical reactivity is limited. The design is based on gluteraldehyde-mediated cross-linking of purified SOD and catalase to purified hemoglobin. See, for example, D'Agnillo et al. (1998) *Nature Biotechnol* 16:667–671 and U.S. Pat. No. 5,606,025, both of which are herein incorporated by reference. The modification has been reported to prevent $H_2O_2$-mediated ferrylhemoglobin formation (D'Agnillo et al. (1998) *Free Rad. Bio. Med* 24:906–912) and reduce hydroxyl radical generation both in vitro, in a rat hind limb model of ischemia-reperfusion injury (D'Agnillo et al. (1998) *Artif. Cells Blood Substit. Immobil. Biotechnol* 25:181–192) and in vivo, in a rat model of intestinal ischemia-reperfusion injury (Razack et al. (1997) *Artif. Cells Blood Substit. Immobil. Biotechnol.* 25:163–180). These studies have led to the proposal that modified hemoglobins with antioxidant activity may reduce the potential toxicity of hemoglobin-based oxygen carriers in certain applications by maintaining the oxygen-carrying ferrous form of hemoglobin and by decreasing the occurrence of potentially harmful hemoprotein-associated free radical species or the release of hemoglobin degradation products which may be harmful to the surrounding tissues.

While the cross-linked polypeptide complex comprising hemoglobin, SOD, and catalase has been suggested to have potential in vivo benefits, the methods taught by U.S. Pat. No. 5,606,025 for the preparation of the modified hemoglobin product comprises combining purified hemoglobin with purified bovine catalase and superoxide dismutase in the cross-linking reaction. There are several practical drawbacks to the addition of enzymes back to purified hemoglobin. First, the addition of bovine or any non-human derived enzymes is potentially a problem based on the immunogenecity associated with the enzymes during human administration. Second, the purification of the enzymes from human blood is costly and may be inhibitory to producing a product economically.

Pyridoxalated hemoglobin polyoxyethylene conjugated (PHP) is a chemically modified, human derived hemoglobin. The PHP molecule is a surface decorated hemoglobin with contains endogenous antioxidant enzyme activities (Privalle et al. (1998) *Free Rad. Bio. Med.* 25:(Suppl. 1)S65 abstr; Privalle et al. (2000) *Acta Physiol. Scand.* 167:(Suppl. 645)P200 abstr.; Privalle et al. (1999) *Free Rad. Bio. Med.* 28:1507–1517 and Talarico et al. (2000) *Biochim. Biophys. Acta* 1476:53–65; all of which are herein incorporated by reference). PHP, in several in vitro models, has been demonstrated to display a decreased reactivity toward hydrogen peroxide-mediated oxidation when compared to unmodified hemoglobin or αα-crosslinked hemoglobin. Hence, the redox reactivity of the hemoglobin preparations can be manipulated and the presence of endogenous antioxidants may reduce the pro-oxidant potential of hemoglobin. Therefore PHP, by virtue of the presence of endogenous red blood cell antioxidants, may function as a cell free hemoglobin with the antioxidant potential of the intact red blood cell, thus preventing or reducing the pro-oxidant potential of hemoglobin.

A serious problem associated with animal or human derived hemoglobin based blood substitutes arises from the possibility of viral contaminants in the modified hemoglobin solution. Virus elimination and inactivation is commonly performed using either chromatography or heat inactivation. However, treatment of hemoglobin solutions using these methods either removes or abolishes the beneficial activity of the antioxidants associated with the hemoglobin molecule.

For instance, prior methods for the synthesis of a chemically modified hemoglobin product employed filtration means that prevented passage of viral particles but also prevented the passage of endogenous antioxidant enzymes. Alternative methods are provided in U.S. Pat. No. 5,741,894 which discloses a method for the preparation of a pharmaceutical grade hemoglobin. U.S. Pat. No. 5,464,814 discloses a process for preparing a tetramer-free, stroma-free, cross-linked, polymerized, pyridoxylated hemoglobin. Both methods employ a filtration step that allows the passage of hemoglobin, endogenous antioxidant enzymes, and viral particles. The viral particles are subsequently inactivated in a heat treatment step that abolishes the activity of both the viral particles and antioxidant enzymes. In other methods, the viral particles are removed along with the antioxidant enzymes by chromatography. See, for example, U.S. Pat. Nos. 5,264,565 and 5,988,361.

Alternatively, U.S. Pat. No. 5,194,590 discloses a method of preparing a modified hemoglobin comprising the lysis of red blood cells and removal of red blood cell stroma by a microporous filtration process that allows hemoglobin and the enzymatic contents of the red blood cells to pass through the filter using a 0.1 µm filter. Following chemical modification, a three step purification process is performed which removes unmodified tetramers and also reduces viral contamination. The additional chromatography step is essential to remove the viral contaminants from the hemoglobin solution, which passed through the 0.1 µm filter.

Because the antioxidant enzymes provide advantageous properties to the modified hemoglobin, methods are needed to prepare purified hemoglobin that is viral free yet still retains antioxidant activity.

SUMMARY OF THE INVENTION

The present invention provides methods and compositions for the separation of hemoglobin molecules and endogenous antioxidant enzymes from red blood cell stroma. The method of separation further reduces the level of potential adventious agents, such that a substanitally viral free hemoglobin/antioxidant solution is produced. Specifically, the present invention provides a method for preparing a modified hemoglobin solution comprising endogenous antioxidant enzymes of the red blood cells. The method comprises contacting a stroma free hemoglobin solution with at least one filtration means that retains viral particles and allows passage of a filtrate comprising hemoglobin and endogenous antioxidant enzymes, chemically modifying the filtrate with an agent, and isolating the modified hemoglobin and antioxidant enzymes. In one embodiment, the method of the present invention is used to synthesize pyridoxalated hemoglobin polyoxyethylene conjugate (PHP).

The present invention also provides a method of preparing a chemically modified hemoglobin. The method consists of contacting a stroma free hemoglobin solution with at least one filtration means, wherein a first filtration means retains viral particles and allows passage of a filtrate comprising hemoglobin and endogenous antioxidant enzymes and the filtrate is substantially free of viral contamination; chemically modifying the filtrate with an agent; and, isolating the modified hemoglobin and antioxidant enzymes.

The present invention further provides a composition comprising a modified hemoglobin solution. The modified hemoglobin solution comprises chemically-modified hemoglobin molecules and at least one endogenous antioxidant enzyme wherein the chemical modification comprises crosslinking with bifunctional activated polyoxyethylene (POE). The endogenous antioxidants present in the solution retain enzymatic activity, and the solution is substantially free of viral contamination.

DETAILED DESCRIPTION OF THE INVENTION

The methods of the present invention provide for the separation of hemoglobin and several endogenous antioxidant enzymes from red blood cell stroma and potential adventitious agents. The purified hemoglobin/antioxidant composition is then subjected to a chemical modification process. The resulting modified hemoglobin/antioxidant composition is subsequently fractionated to remove unmodified hemoglobin species and residual reactants, formulated in electrolytes and rendered sterile. The resulting modified hemoglobin product is substantially free of viral contamination and contains at least one endogenous antioxidant enzyme that retains antioxidant activity.

The methods of the present invention provide a novel means to prepare a chemically modified hemoglobin solution which retains the activity of at least one endogenous antioxidant enzyme and is substantially free of viral contaminants. Specifically, the present invention employs a unique filtration step during the hemoglobin purification process that offers a means to substantially decrease viral contamination of a modified hemoglobin solution and retain endogenous antioxidant enzymes.

The filtration means of the present invention provides a novel method of preparing a chemically modified hemoglobin. The method comprises: (a) contacting a stroma free hemoglobin solution with at least one filtration means, wherein a first filtration means retains viral particles and allows passage of a substantially viral free filtrate comprising hemoglobin and endogenous antioxidant enzymes; (b) chemically modifying the filtrate with an agent; and, (c) isolating a composition comprising modified hemoglobin and endogenous antioxidant enzymes, wherein at least one endogenous antioxidant enzyme retains enzymatic activity.

Furthermore, the filtration means of the present invention provides a method of preparing a chemically modified hemoglobin consisting of: (a) contacting a stroma free hemoglobin solution with at least one filtration means, wherein a first filtration means retains viral particles and allows passage of a filtrate comprising hemoglobin and endogenous antioxidant enzymes and the filtrate is substantially free of viral contamination; (b) chemically modifying the filtrate with an agent; and, (c) isolating a composition comprising modified hemoglobin and endogenous antioxidant enzymes.

As used herein, the "first filtration means" used in the methods of the present invention comprises an ultrafiltration step that allows for the isolation of an ultrafiltrate comprising hemoglobin molecules and at least one endogenous antioxidant enzyme that is substantially free of viral contamination. By "substantially free of viral contamination" is intended a solution having a viral titer of less than 1 infectious unit/ml.

The first filtration means of the present invention reduces the level of viral contamination in the resulting filtrate. In the methods of the present invention, a reduction in viral contamination encompasses any decrease in the overall level of viral particles and/or a decrease in the activity of the viral particles. The ultrafiltration means of the present invention reduces the levels of enveloped and/or non enveloped viruses, including for example, viral particles ranging in size from 120–200 nm (such as Herpes Simplex types I and II, Herpes virus 6 and 7, Epstein-Barr virus and Cytomegalovirus), 80–100 nm (such as HIV, HTLV-I and II), 50–70 mn (such as hepatitis G, hepatitis C, HCV, and DHBV), and 25–30 nm (non-enveloped viruses such as hepatitis A).

As defined herein, a reduction in the level of active viral particles encompasses a viral removal clearance factor following the first filtration means that is greater than 3, 4, 5, 6, 7, 8, 9, 10 or more log units as measured by counting plaque forming units (PFUs). The decrease in the viral titer can be determined by assaying the starting materials, process intermediates, and final product by standard plaque forming assays known in the art. See, for example, Bechtel et al. (1988) *Biomat Art Cells Art Org* 16:123–128, herein incorporated by reference. Alternatively, a reduction in active viral particles encompasses a decrease in viral titer, as determined by $TCID_{50}$ values. $TCID_{50}$ is defined herein as the tissue culture infectious dose resulting in the death of 50% of the cells.

Other assays to determine if the resulting filtrate is substantially viral free (i.e., has a reduced level of viral particles) are well known in the art. For example, the absence of viral DNA can be detected by DNA hybridization techniques using virus specific probes for Hepatitis B Virus, Cytomegalovirus, Herpes Simplex Virus and Epstein-Barr Virus. DNA can be extracted from the filtrate, subjected to southern analysis, and probed with $^{32}P$-labeled or biotin-labeled DNA specific for the virus. Viral particle contamination can also be detected by ELISA methods known to detected specific viral antigens such as core proteins.

Furthermore, the substantially viral free solution produced following the first filtration means of the present invention is characterized by not inducing pathophysiological effects characteristic of viral infection upon in vivo administration to a subject (i.e., a mammal, preferably a mouse, bovine, pig, monkey, human, etc.). For instance, physiological symptoms for non-A and non-B hepatitis include monitoring aspartate aminotransferase activity, alanine aminotransferase activity, and liver physiology (as assayed by light or electron microscopy) over a 4, 10, 14, or 24 week period. Pathophysiological effects that result from infection of other viral particles are well known in the art. Hence, as used herein, a substantially viral free solution is noninfectious, such that the solution can be transfused or manipulated without harming or infecting anyone exposed thereto.

The first filtration means used in the methods of the present invention further allows for the isolation of a filtrate comprising a hemoglobin molecule and at least one endogenous red blood cell enzyme. Of particular interest are endogenous antioxidant enzymes. By "endogenous" antioxidant enzyme or polypeptide is intended any antioxidant polypeptide that is released from the red blood cells during the red blood cell stroma isolation procedure. As used herein "endogenous" antioxidant enzymes do not encompass antioxidant enzymes purified from human or animal red blood cells or recombinantly expressed antioxidant enzymes that are added back to the hemoglobin solution during the modification process following the lysis step. Endogenous antioxidant enzymes of particular interest include superoxide dismutase, catalase, and glutathione peroxidase.

The antioxidants of the red blood cells are useful in eliminating activated oxygen species such as hydrogen peroxide and superoxide that are generated in the body during injury. Further, each subunit of hemoglobin contains an iron heme group that must exist in the ferrous state in order for the hemoglobin to transport oxygen. Antioxidants efficiently assist in maintaining the hemoglobin in a ferrous state and prevent the occurrence of potential harmful hemoprotein-associated free radical species or the release of hemoglobin degradation products. Hence, the presence of the enzymatically active antioxidants throughout the isolation and modification methods of the present invention will help to reduce the level of methemoglobin formation in the final modified product and during the product's circulation in a subject.

The first filtration means of the present invention results in a filtrate comprising antioxidant activity (i.e., catalase, glutathione peroxidase, or superoxide dismutase). The activity of individual antioxidants can be measured by commonly used methods. For instance, catalase is a 240,000 to 250,000 molecular weight protein with a specific activity of 70,000 to 80,000 U/mg. One unit of catalase activity corresponds to the amount of enzyme that decomposes 1 $\mu$mol $H_2O_2$ per minute at pH 7.0 and 25° C. Methods for measuring catalase activity are known in the art and are described in Beers and Sizer (1952) *J. Biol. Chem.* 195:133–140. Briefly, a catalase-containing solution is added to a Curette containing hydrogen peroxide in 50 mM sodium phosphate buffer. The rate of disappearance of hydrogen peroxide is measured over a 30 second period spectrophotometrically. See, for example, U.S. Pat. No. 5,606,025 and D'Agnillo et al. (1998) *Nature Biotechnology* 16:667–671, all which are herein incorporated by reference. In the methods of the present invention, the filtrate can retain catalase activity of about 5,000 units/ml; 6,000 units/ml; 7,000 units/ml; 9,000 units/ml; 12,000 units/ml; 14,000 units/ml; 16,000 units/ml; 20,000 units/ml; 24,000 units/ml; 28,000 units/ml or greater. Alternatively, catalase activity can range between about 5,000 to 30,000 units/ml, 7,000 to 25,000 units/ml or 7,800 to 23,000 units/ml.

Superoxide dismutase (SOD) is an antioxidant enzyme of 32,000 molecular weight with a specific activity of 4,000 U/mg. One unit of SOD activity is defined as the amount of enzyme that inhibits the initial rate of cytochrome c reduction by 50%. Assays to measure activity are described in Crapo et al. (1978) *Methods of Enzymology* 52: 382–387. Briefly, a reagent solution consisting of xanthine and cytochrome c can be added to the SOD containing solution. Free catalase is also added to the reaction to prevent any interference resulting from a hemoglobin-hydrogen peroxide interaction. The rate of cytochrome c reduction can be monitored spectrophotometrically at 550 nm. Cytochrome c reduction assays are described in detail in U.S. Pat. No. 5,606,025 and D'Agnillo et al. (1998) *Nature Biotechnology* 16:667–671; both of which are herein incorporated by reference. Other assays used to measure the level of SOD activity include, for example, the inhibition of nitro blue tetrazolium reduction (Beyer et al. (1987) *Anal Biochem* 161: 559–566, herein incorporated by reference).

Carbonic anhydrase is a 84,000 molecular weight protein with a specific activity of greater than 700 U/mg. One unit of carbonic anhydrase activity is defined as the amount of enzyme that causes the pH of a 20 mM tris Buffer to drop from 8.3 to 6.3 per minute at 0C. Assays to measure the level of carbonic anhydrase can be found, for example, in Wilber et al. (1948) *J. Biol. Chem.* 250:3523, herein incorporated by reference.

Glutathione peroxidase is a 29,000 molecular weight protein with a specific activity of greater than 3000 U/mg. One unit of glutathione peroxidase activity catalyzes the oxidation by $H_2O_2$ of 1 $\mu$mol reduced glutathione to oxidized glutathione per minute at pH 7.0 and 25° C. Assays to measure the level of glutathione peroxidase include, for example, those set forth in Mannervik et al. (1985) *Methods in Enzymol* 113:490 and Meister et al. (1983) *Ann. Review Biochem* 52:711; both of which are herein incorporated by reference.

The overall level of endogenous antioxidant activity can be assayed by monitoring the absorbance spectra of the hemoglobin molecule following oxidative challenge. For instance, hydrogen peroxide can be added to the filtrate and the absorbance spectra (450 nm–700 nm) can be recorded over time to monitor the reactions of hydrogen peroxide or resultant oxygen free radicals with the hemoglobin components of the isolated hemoglobin solution. The presence of antioxidant enzymes will result in a decreased level of heme moiety degradation and be reflected in the spectra analysis. Similar oxidative challenges can be performed using a xanthine/xanthine oxidase superoxide/$H_2O_2$ generating system.

For example, methemoglobin formation following $H_2O_2$ challenge can be assayed by the addition of 200 $\mu$M $H_2O_2$ to a hemoglobin solution (20 $\mu$M heme). Methemoglobin formation will be reflected in a decrease in absorbance at 541 mn and 577 nm. The level of antioxidant enzymes in the filtrate following the first filtration means will be such as to prevent less than about 50%, 40%, 30%, 20%, 15%, 10%, 9%, 8%, 7%, 6%, 5%, 4%, 3%, 2%, and 1% of the hemoglobin from converting to methemoglobin as compared to a purified, antioxidant free, hemoglobin solution. Alternatively, the level of antioxidant enzymes in the filtrate following the first filtration means will be such as to prevent less than about 50% to about 5%, about 20% to about 1%, about 10% to about 1% or about 5% less than 1% of the hemoglobin from converting to methemoglobin as compared to a purified, antioxidant free, hemoglobin solution.

Similarly, the presence of ferrylhemoglobin formation following $H_2O_2$ treatment of the filtrate of the present invention can be detected spectrophotometrically after addition of $Na_2S$ that results in subsequent formation of sulfhemoglobin. A distinct peak at 620 nm characterizes this hemoglobin species. The level of antioxidant enzymes in the filtrate following the first filtration means will be such as to prevent less than about 50%, 40%, 30%, 20%, 15%, 10%, 9%, 8%, 7%, 6%, 5%, 4%, 3%, 2%, and 1% of the hemoglobin from converting to sulfhemoglobin as compared to a purified, antioxidant free, hemoglobin solution. Alternatively, the level of antioxidant enzymes in the filtrate following the first filtration means will be such as to prevent less than about 50% to about 5%, about 20% to about 1%, about 10% to about 1% or about 5% less than 1% of the hemoglobin from converting to sulfhemoglobin as compared to a purified, antioxidant free, hemoglobin solution. Such methods to assay the level of antioxidant enzyme activity are described in detail in Privalle et al. (2000) *Free Rad. Biol. Med* 28:1507–1517, herein incorporated by reference.

I. The Process

As described above, the present invention provides a method of preparing a chemically modified hemoglobin comprising: (a) contacting a stroma free hemoglobin solution with at least one filtration means, wherein a first filtration means retains viral particles and allows passage of a filtrate comprising hemoglobin and endogenous antioxidant enzymes and the filtrate is substantially free of viral contamination; (b) chemically modifying the filtrate with an agent; and, (c) isolating a composition comprising modified hemoglobin and endogenous antioxidant enzymes, wherein at least one endogenous antioxidant retains enzymatic activity.

A. Isolation of Stroma Free Hemoglobin:

The preferred starting material in the process of the present invention is outdated human blood. However, all the methods of the present invention can be used with other mammalian blood (i.e., bovine, porcine, ovine) with only minor modifications which are well within skill in the art. Preferably, the blood used in the methods of the invention is not more than 8 weeks past the expiration date on the bag. Concentrated red blood cells are washed to remove plasma components. The washed red blood cells are subsequently contacted with a hypotonic solution. Release of the hemoglobin and endogenous antioxidant enzyme result. See, for example, U.S. Pat. Nos. 4,412,989 and 5,264,555, both of which are herein incorporated by reference. Other methods for the isolation of stroma-free hemoglobin solution include the disruption of red blood cells through mechanical degradation. See, for example, U.S. Pat. No. 5,296,465.

A stoma-free hemoglobin is prepared from the lysed red blood cells. As defined herein, "stoma-free hemoglobin" is a solution of hemoglobin and antioxidant enzymes with a reduced level of stromal contaminates, including, for example, DNA, phospholipids, residual blood group antigens, and serum proteins. The level of contaminating red blood cell stroma contaminants in the stroma-free hemoglobin is reduced by at least about 40%, 50%, 60%, 70%, 80%, 90%, 91%, 92%, 93%, 94%, 95%, 96%, 97%, 98%, 99%, or greater.

Any method that removes stromal components from the hemoglobin, but does not remove the antioxidant proteins or deplete antioxidant enzyme activity can be used in the methods of the present invention. For example, the lysed red blood cell solution can be clarified by passage through a 0.1 $\mu$m or 0.2 $\mu$m cellulose acetate filter unit, such as those manufactured by Sartorious. Alternatively, a tangential flow (TFF) flat sheet membrane 0.45 $\mu$m, 0.2 $\mu$m, or 0.1 $\mu$m with open channels which allow red blood cells to flow freely (such as Pall Filtron's Supor biplanar channel membrane or Sartorious's open channel membrane); or, a 0.45$\mu$ to 0.1$\mu$ hollow fiber membrane or TFF, can be used. Other filters of these pore sizes made from PVDF or polyethersulfone, for instance, those manufactured by Pall, Millipore, and Sartorious can also be used. Alternatively, washing can be performed on a 0.65 $\mu$m, 0.45 $\mu$m, or 0.2 $\mu$m membrane (hollow fiber or TFF) and hemoglobin purification is carried out on a 0.1 $\mu$m membrane.

B. Purification of Stroma Free Hemoglobin

The stroma free hemoglobin solution is next contacted with a "first filtration means." As discussed above, the first filtration means is an ultrafiltration membrane that retains viral particles and allows passage of an ultrafiltrate comprising hemoglobin and endogenous antioxidant enzymes. The ultrafiltrate is characterized as retaining the activity of at least one endogenous antioxidant enzyme and having a significant reduction in viral load.

It is recognized that the retention of viruses and proteins differ for membranes from manufacturer to manufacturer. Thus, any ultrafiltration means that produces an ultrafiltrate that is substantially free of viral contamination and contains enzymatically active endogenous antioxidant polypeptides can be used in the methods of the present invention. For instance, the stroma free hemoglobin can be passed through a 500,000 molecular weight cutoff polysulfone membrane with 1 mm lumen diameter (AG-Technology). The lumen diameter of this membrane can be varied in the methods of the invention.

Other manufacturer membranes in the TFF mode could also be used as the first filtration means in the methods of the invention. Alternatively, a membrane which is intermediate in pore size such as the Pall filtron 150,000 molecular weight cutoff membrane or even other manufacturer's membranes such as the Sartorious 100,000 molecular weight cutoff membrane can be used in the ultrafiltration step of the present invention. Now that the present invention has demonstrated that a filtration means can be used to prepare a substantially viral free modified hemoglobin solution retaining antioxidant activity, it is well within skill in the art to identify other ultrafiltration means and operating conditions (i.e., flow rate, transmembrane pressure, and crossflow) that optimizes hemoglobin and antioxidant enzyme passage and significantly reduce viral contamination. Examples of assays for antioxidants and viral activity are described herein.

It is further recognized that a "second filtration means" can find use in the methods of the present invention. This second filtration step comprises dead-end filtration that results in a further reduction in the level of active viral particles and continues to allow the passage of hemoglobin and endogenous antioxidant enzymes. A reduction in the level of active viral particle using the second filtration means encompasses a 3, 4, 5, 6, 7, 8, 9, 10 or more log unit reduction as measured by PFUs or $TCID_{50}$. Any dead-end filtration means can be used for the second filtration step in the methods of the present invention. For instance, the purified stroma free hemoglobin can be passed through a cartridge filter, such as a Pall DV-50 or DV-20. Other membranes of interest for this supplemental filtration step include the Millipore's Viresolve NFR filter.

The isolated filtrate from either the first or second filtration means is concentrated to achieve the desired hemoglobin concentration. A Pall Filtron 10,000 molecular weight cutoff T-screen Omega series membrane can be used in this step. However, other membranes could also be used so long as the pore size is small enough to prevent passage of hemoglobin and enzymes such as superoxide dismutase. Examples are Millipore 5,000 or 10,000 Biomax TFF membranes; Sartorious TFF 10,000 membranes; and, AG Technology 5,000 hollow fiber membranes. The solution is washed with buffer to remove small molecular weight contaminants while minimizing hemoglobin and enzyme passage. The concentrated solution is diluted with buffer and is filtered through a 0.2 $\mu$M filter. Purified stroma free hemoglobin ready for chemical modification is obtained.

C. Chemical Modification of the Ultrafiltrate:

Hemoglobin is a tetramer with two $\alpha$ subunits and two $\beta$ subunits. When purified, unmodified hemoglobin is infused into the body, the tetramer ($\alpha1\beta1\alpha2\beta2$) breaks down into toxic dimers ($\alpha1\beta1$ and $\alpha2\beta2$), which are rapidly filtered by the kidneys into the renal tubules, where high concentrations become toxic. Therefore, the native "unmodified" form of hemoglobin is too toxic to be used as a blood substitute, and thus methods have been developed to modify the hemoglobin molecule and reduce its toxicity. The hemoglobin molecule contains reactive amino groups. Chemical modification of these reactive amino groups result in a chemically modified hemoglobin. Hence, the substantially viral free solution comprising hemoglobin and endogenous antioxidant enzymes produced by the methods described above, can be subsequently modified to produce a modified hemoglobin solution.

As used herein, "chemically modifying" the ultrafiltrate encompasses any structural modification to the hemoglobin and/or antioxidant molecules that alter shape, size, function or any physical characteristics of the polypeptides. The chemical modifications useful in the methods of the present invention include, for example, cross-linking or conjugation using any agent and method known in the art.

By conjugation is intended the attachment of soluble polymers to both the hemoglobin and endogenous antioxidant enzymes. The conjugating agents used in the present invention may be monofunctional or bifunctional and include, for example, soluble polymers such as dextran, inulin, polyoxyethylene, and polyethylene glycol (PEG).

By cross-linking is intended the use of a bifunctional agent that forms either intermolecular or intramolecular linkages. Hence, a cross-linking modification can result in intermolecular linkages between the endogenous antioxidant enzymes and the hemoglobin subunits. Cross-linking may further comprise the establishment of intramolecular linkages between hemoglobin dimers. An intramolecular cross-link does not change the molecular size of the hemoglobin tetramer or the antioxidant enzyme, while an intermolecular cross-linking event results in the polymerization or tethering of polypeptides and an enlarged molecular weight.

Hence, a solution comprising the "modified hemoglobin" of the present invention can comprise any combination of the following modified complexes:
 (a) intermolecular cross-linked products including:
   antioxidant:antioxidant
   hemoglobin:hemoglobin
   antioxidant:hemoglobin
 (b) intramolecular cross-linked products including:
   hemoglobin $\alpha1\beta1$:hemoglobin $\alpha2\beta2$
 (c) conjugated products including:
   hemoglobin: soluble polymer
   antioxidant:soluble polymer
   hemoglobin:antioxidant:soluble polymer Agents and methods for the generation of a solution comprising any of the above modified complexes or combinations thereof are known in the art. For instance, non-specific bifunctional agents can be used to cross-link the reactive amino groups of hemoglobin and the antioxidant enzymes producing a solution comprising a chemically modified polymerized hemoglobin and antioxidant enzyme complex. In preparing such a complex, any agent previously reported for establishing an intermolecular cross-link between two polypeptides can be used. Such non-specific bi-functional agents include, for example, sebacyl chloride (Chang et al. (1964) Science 146:524–525 and Chang et al. (1972) Artificial Cells), glutaraldehyde (Chang et al. (1971) Biochem. Biophys. Res. Commun. 44: 1531–1533; U.S. Pat. No. 5,194,590), diaspirin derivatives (U.S. Pat. No. 4,529, 719), polyaldehydes and bifunctional polymers.

In one embodiment of the present invention, the bi-functional cross-linking/conjugating agent is N-hydroxysuccinimide diester of oc-carboxymethyl $\omega$-carboxymethoxypolyoxyethylene (POE). The use of this particular cross-linking agent is discussed in greater detail in the Experimental Section and Iwashita et al. (1995) Artificial Red Blood Cells John Wiley & Sons; and, U.S. Pat. Nos. 4,301,144; 4,412,989; 4,670,417; all of which are herein incorporated by reference. Other bifunctional reagents include, for example, activated polymers, such as other PEG derivatives, inulin or dextran. In addition, a combination of bifunctional PEG derivatives and monofunctional PEG derivatives may be used to attain the desired molecular weight distribution of the modified hemoglobin.

Alternatively, zero-link technology can be used to form a cross-linked complex. The zero-link technology involves the activation of COOH groups on the surface of a polypeptide, followed by a reaction with an available $NH_2$ group on the surface of adjacent hemoglobin or antioxidant molecules. See, for example, U.S. Pat. No. 5,998,361.

It is understood in the art that altering specific parameters of the chemical modification protocols can control the level of chemical modification. The degree of chemical modification desired will be such as to produce a modified hemoglobin solution that does not produce pathophysiological effects implicated with the intravenous administration of unmodified hemoglobin solutions (i.e., vasoconstriction, renal toxicity, hemoglobinuria, etc.). Further, the level of chemical modification will optimize the half-life of the modified hemoglobin and antioxidant polypeptides and the hemoglobin $P_{50}$-value. By "half-life" is intended the period of time following administration in which the concentration of the polypeptide falls to half of its initial levels. The term $P_{50}$ is recognized in the art to describe the interaction between oxygen and hemoglobin and represents the partial pressure of $O_2$ at a 50% saturation of hemoglobin. This interaction is frequently represented as an $O_2$ dissociation curve with % saturation of hemoglobin plotted against mmHg or torr.

Any of the in vitro methods discussed previously may be used to determine the level of antioxidant activity in the final chemically modified hemoglobin solution. In addition, the presence of antioxidant activity in the final modified product of the present invention can also be assayed in vivo. For instance, a rat model of in vivo intestinal ischemia-reperfusion can be used. Following an intestinal ischemic event, the hemoglobin solution comprising a hemoglobin/antioxidant product of the invention can be perfused without recirculation. Portal vein effluent samples can be collected and the generation of free radicals, as assayed by the hydroxylation of 4-hydroxybenzoate to 3,4-dihydroxybenozate (3,4 DHBA) can be determined by HPLC using electrochemical detection (D'Agnillo et al. (1998) *Nature Biotechnology* 16: 667–671).

Hence, the filtration means used in the methods of the present invention results in a chemically modified hemoglobin containing about a 10%, 20%, 30%, 40%, 50%, 60%, 70%, 80%, 90%, 100%, 110%, 120%, 130%, 150%, 160%, 170%, 180%, 190%, 200%, 250% or greater increase in endogenous antioxidant activity per unit of hemoglobin found in red blood cells. Alternatively, the chemically modified hemoglobin solution may comprise about a 10%–40%, 40%–80%, 80%–120%, 120%–160%, 160%–200%, 200%–250%, or alternatively 50%–200% increase in antioxidant activity per unit of hemoglobin found in red blood cells. This increase in antioxidant activity may reflect an increased activity of a single antioxidant enzyme (i.e., SOD, catalase, glutathione peroxidase, etc.), or alternatively, the increase can reflect an overall elevation in antioxidant activity.

The level of antioxidant activity in the final modified hemoglobin product will be such as to prevent less than about 50%, 40%, 30%, 20%, 15%, 10%, 9%, 8%, 7%, 6%, 5%, 4%, 3%, 2%, and 1% of the hemoglobin from converting to ferrylhemoglobin and/or methemoglobin as compared to a modified hemoglobin solution lacking antioxidant enzymes. Alternatively, the level of antioxidant enzymes in the final modified hemoglobin product will be such as to prevent less than about 50% to about 5%, about 20% to about 1%, about 10% to about 1% or about 5% less than 1% of the hemoglobin from converting to ferrylhemoglobin and/or methemoglobin as compared to a modified hemoglobin solution lacking antioxidant enzymes.

It is further recognized that a second modifying agent may be used to establish intermolecular cross links in the hemoglobin tetramer, such as bis-(N-maleimido-methyl)ether and bis-(3,5-dibromosalicyl)fumarate. See for example, Bunn et al. (1969) *J. Exp. Med.* 129:909–924 and Walder et al. (1979) *Biochemistry* 18:4265–4270.

Depending on the red blood source, it may be desirable to derivatize in the beta cleft of the hemoglobin molecule with pyridoxal-5'-phosphate (PLP) prior to the chemical modification procedure discussed above. Methods of pyridoxylation increase the $P_{50}$ of the complex and are commonly known by one of skill in the art. See, for example, U.S. Pat. No. 5,194,590. Beta cleft modification can also be achieved using dialdehyde o-raffinose. See, for example, U.S. Pat. No. 4,857,636 and Adamson et al. (1998) *Blood Substitutes: Principles, Methods, Products, and Clinical Trials* Vol II 62–79.

Further, it is recognized that the chemical modification and β-cleft derivatization discussed above can be carried out under deoxygenated conditions. One method of deoxygenation comprises the continuous bubbling of $N_2$ gas during the modification reaction. Several other techniques are available in the art for deoxygenation and re-oxygenation of hemoglobin solutions including, for example, membrane exchanges like Liqui-cell from Hoechst Celanese and thin layer techniques for countercurrent gas exchange.

The chemically modified hemoglobin made by the methods of the present invention can be encapsulated inside an artificial cell. Such methods are known in the art including, for example, encapsulation into artificial red blood cells with artificial membranes, small lipid-membrane artificial red blood cells prepared using lipid-membrane liposomes, and biodegradable-polymer hemoglobin nanocapsules (i.e., polylactic acid encapsulation). See, for example, Chang et al. (1988) *Biomater. Artif. Cells Artif. Organs* 16:1–9; Chang et al. (1968) *Nature* 218:242–245; Rudolph et al. (1998) *Blood substitutes: Principles, Methods, Products, and Clinical Trials* (Vol II) 197–205; and Tsuchida et al. (1995) *Artificial Red Cells*, John Wiley & Sons.

D. Isolation and Formulation of the Modified Hemoglobin/Antioxidant Complex

Following the chemical modification process, the hemoglobin/antioxidant solution can be isolated by any method known in the art, so long as, the activity of the antioxidant activity is not destroyed. Such methods can include, for example, chromatography or filtration. For instance, the conjugated hemoglobin solution can be isolated by diafiltration through using a Pall-Filtron TFF 100,000 molecular weight cutoff T-screen Omega series membrane. Other manufacturer's 100,000 molecular weight membranes can be used in the isolation step. A smaller pore size membrane such as a Pall-Filtron 85,000 or 70,000 molecular weight cutoff membrane can be used if the washing process is modified. Accordingly, the solution is subsequently washed with purified water or a suitable buffer to remove residual reactants and to reduce the unmodified hemoglobin content.

The washed modified hemoglobin solution is removed from the membranes and formulated in water or Plasma-Lyte A. Electrolytes are added to make the solution iso-osmotic compared to blood. Alternatively, the solution may be formulated by diafiltration against the final formulation buffer. A substantially viral free modified hemoglobin solution comprising a conjugated hemoglobin:antioxidant complex results.

The modified hemoglobin may also be lyophilized to form a preparation for use as a drug. While the antioxidant enzymes present in the modified complex will likely serve as stabilizing agents and inhibit the production of methemoglobin and insoluble material, other agents commonly used in the art can be added. Such compounds include sodium sulfite, sodium bisulfite and iron (II) sulfate, and amino compounds such as EDTA and salts thereof. Monosaccharides such as D-galactose and D-glucose; disaccharides such as sucrose, maltose and lactose; and amino acids are also used as effective stabilizing agents. Methods of freeze-dried preparations of modified hemoglobin solutions can be found in, for example, U.S. Pat. No. 4,670,417, herein incorporated by reference.

In one embodiment, the methods of the present invention are used for the synthesis of PHP. PHP synthesized by the methods described above is substantially viral free and comprises hemoglobin covalently cross-linked to endogenous, enzymatically active, antioxidant enzymes. The PHP synthesized by these methods contains an antioxidant profile similar to the intact red blood cell. The PHP typically contains greater than 90% of the catalase and SOD activity per unit of hemoglobin found in RBC. The endogenous antioxidants that remain associated with the modified hemoglobin in PHP may attenuate redox activity, reduce pro-oxidant potential, and improve the nitric oxide scavenging properties of the modified hemoglobin. Thus the modified PHP may have beneficial effects in the treatment of certain disease states.

Methods of PHP synthesis and characterization are provided in the Experimental section. Further details describing the synthesis and characterization process can be found in, for example, U.S. Pat. Nos. 4,301,144; 4,421,989; 4,670,417; Iwashita et al (1995) *Artificial Red Blood Cells* John, Wiley & Sons; Talarico et al. (2000) *Biochimica* 1476: 53–65; and Privalle et al. (2000) *Free Rad. Biol. Med.* 28:1507–1517; all of which are herein incorporated by reference.

II. Methods of Use

The present invention further encompasses methods for using the modified hemoglobin of the invention for medical treatment by administering intravenously to a mammal needing such treatment a therapeutically effective amount of the modified hemoglobin in conjunction with a nontoxic, pharmaceutically acceptable carrier. It is recognized that a pharmaceutically effective amount varies in relation to the therapy desired for the particular disease or medical condition being treated. It is further recognized that typical dosage parameters will also vary depending on, for example, the body weight of the patient. It would be apparent to one skilled in the art how to select a dosage amount in any given situation. Techniques and formulations for administering the compositions comprising the modified hemoglobin generally may be found in *Remington's Pharmaceutical Sciences*, Meade Publishing Col., Easton, Pa., latest edition, herein incorporated by reference.

The modified hemoglobin solutions of the present invention may be utilized in, for example, the treatment of trauma, myocardial infarction, stroke, acute anemia and oxygen deficiency disorders such as hypoxemia or hypoxia due to impairment or failure of the lung to fully oxygenate blood. See for example, U.S. Pat. Nos. 5,733,896 and 6,090,779, both of which are herein incorporated by reference. Furthermore, the modified hemoglobin of the present invention can be used as a blood substitute and blood expander. Hence, as a blood expander, the modified hemoglobin solution finds use in alleviating anaphylactic and allergic shock, replacing plasma lost after burns, and in volume deficiency shock. The modified hemoglobin solution of the present invention finds further use in replacing blood lost occurring during acute hemorrhage, during surgical operations, in resuscitation procedures after accidental blood loss, for supplying oxygen, and generally to maintain blood volume in related conditions. See, for example, U.S. Pat. No. 5,905,141 herein incorporated by reference. Additionally, the blood substitute of the present invention may be used as an artificial oxygen exchange solution in conventional oxygenators.

In one embodiment, the modified hemoglobin solution of the present invention is use for the treatment of systemic hypotension or septic shock induced by internal nitric oxide production. Such internal nitric oxide production may result from the treatment of an animal with a cytokine, as in the case of systemic hypotension. Alternatively, the modified hemoglobin may be used for the treatment of systemic hypotension in a patient induced by chemotherapeutic treatment. In septic shock, the production of nitric oxide results from the exposure of an animal to a bacterial endotoxin. Viral, fungal or enterotoxin-producing bacteria may also be found to directly or indirectly induce NO overproduction alleviatable by administration of the modified hemoglobin of the present invention. In one embodiment, the hemoglobin is administered intravascularly. The modified hemoglobin solution of the present invention can also be used for the treatment of SIRS shock and rheumatoid arthritis. The amount of modified hemoglobin administered, the therapeutically effective amount, is an amount sufficient to bind to the excess nitric oxide present, thus removing free nitric oxide from circulation. Such an effective amount can be determined by one of skill in the art. See, for example, U.S. Pat. Nos. 5,674,836; 5,296,466; 5,612,310; and Bone et al. (1998) *J. Appl. Physiol.* 84:1991–1998; Kilboum et al. (1997) *The Yearbook of Intensive Care and Emergency Medicine*, Berlin:Springer-Verlag 230–239; and Bone et al. (1997) *Crit. Care Med.* 25:1010–1018; all of which are herein incorporated by reference.

The modified hemoglobin used in the present invention can be mixed with a pharmaceutically acceptable carrier. The pharmaceutical carriers, include for example, physiologically compatible buffers as Hank's or Ringer's solution, physiological saline, a mixture consisting of saline and glucose, heparinized sodium-citrate-citric acid-dextrose solution, and the like. The hemoglobin for use in the methods of the present invention can be mixed with colloidal-like plasma substitutes and plasma expanders such as linear polysaccharides (e.g., dextran), hydroxyethyl starch, balanced fluid gelatin, and other plasma proteins. Additionally, the modified hemoglobin may be mixed with water soluble and physiologically acceptable polymeric plasma substitutes, examples of which include polyvinyl alcohol, poly(ethylene oxide), polyvinylpyrrolidone, and ethylene oxide-polypropylene glycol condensates and the like.

The following examples are presented to illustrate a best mode and preferred embodiments of the present invention and are not meant to limit the claimed invention unless otherwise specified.

Experimental

EXAMPLE 1

Isolation of a Substantially Viral Free Hemoglobin/ Antioxidant Solution

A. Isolation of Stroma Free Hemoglobin:

Prior to processing, red blood cells are aseptically pooled into a sanitized process vessel and sampled for analysis of pH, hemoglobin concentration and methemoglobin content. Before release for further processing, the criteria set forth in Table 1 are met.

TABLE 1

Inprocess Specifications for Pooled Red Blood Cells

| Test | Method | Specification |
| --- | --- | --- |
| PH | pH meter | 6.0–7.0 |
| Hemoglobin Concentration | Co-Oximeter | >150 mg/ml |
| Methemoglobin Content | Co-Oximeter | <3% |

Red blood cells are diluted 2-fold with pH 7.4, 50 mM sodium phosphate buffer/150 mM sodium chloride buffer (Buffer A). The diluted red blood cells are diafiltered with 7 volumes of the same buffer on the membrane. The red blood cells are concentrated to 70% of their original volume and water is added to reduce the osmolarity of the solution. The hemoglobin is released from the red blood cells by washing the cells with 3 volumes of water. The hemoglobin solution is clarified by passage through a 0.1μ cellulose acetate filter unit (Sartorious), resulting in stroma free hemoglobin (SFH).

B. Ultrafiltration of Stoma Free Hemoglobin:

Stroma free hemoglobin is passed through a 500,000 molecular weight cutoff membrane (AG Technology 500,000 molecular weight cutoff polysulfone membrane with 1 mm lumen diameter) to remove residual red blood cell membrane fragments and viral particles (see viral removal and inactivation studies in Example 4). Preferred parameters for the ultrafiltration step include a cross flow rate of 1.4 to 2.0 L/min·ft$^2$ and an inlet pressure of 12 to 16 PSIG and a TMP of 6 to 9 PSIG.

The solution is concentrated and washed at a volume of approximately 25% of the start volume. The wash is performed with Buffer A. Typically 1 to 3 volumes of Buffer A are used. The volume used is chosen to provide acceptable recovery of the hemoglobin and enzymes from stroma free hemoglobin.

A second filtration step can be used as a supplemental virus removal step. The ultrafiltrate is passed through a Pall DV-50 or DV-20 cartridge filter that is effective at allowing passage of hemoglobin and enzymes. Alternatively, a Millipore's Viresolve NFR filter can be used. Typically, the solution is filtered by applying a pressure to the fluid of 20 to 50 PSIG. The flow rate of the filtrate is dependent on the pressure and filter used. The resulting ultrafiltrate has a reduced viral load.

Purified stroma free hemoglobin is the starting material for chemical modification and must meet in-process specifications for pH, conductivity and hemoglobin concentration in order to assure optimal parameters for further processing. It must possess a low endotoxin content and minimal microbial contamination. Its purity is monitored by detection of contaminants such as residual blood group antigens, serum proteins, and phospholipids. The integrity of the hemoglobin is assessed by analyzing the methemoglobin content and the $P_{50}$. The specifications for each of these analyses are shown in Table 2.

The purified stroma free hemoglobin is concentrated and diafiltered on a 10,000 polysulfone membrane. Specifically, a Pall Filtron 10,000 molecular weight cutoff T-screen Omega series membrane is used until a hemoglobin concentration of 100 mg/mL is attained. The solution is washed with 3 volumes of Buffer A to remove small molecular weight contaminants. Hemoglobin and enzyme passage is minimized. The concentrated solution is diluted to 60 mg/mL with Buffer A and is filtered through a 0.2 μM filter. Purified stroma free hemoglobin ready for chemical modification is obtained.

TABLE 2

Inprocess Specifications for Purified Stroma Free Hemoglobin

| Test | Method of Analysis | Specification |
|---|---|---|
| PH | pH meter | 7.4 ± 0.5 |
| Conductivity | Conductivity meter | 10–17 mS/cm |
| Hemoglobin Concentration | Co-Oximeter | 55–65 mg/ml |
| Methemoglobin Content | Co-Oximeter | <5% |
| $P_{50}$ | Hemox | 9–14 mm Hg |

TABLE 2-continued

Inprocess Specifications for Purified Stroma Free Hemoglobin

| Test | Method of Analysis | Specification |
|---|---|---|
| Sulfhemoglobin Content | Spectrophotometric | <3% |
| Endotoxin | LAL | <1.00 EU/ml |
| Residual Serum Proteins | Western Blot or ELISA | <1.0% HAS<br><0.3% IgG |
| Phosphatidylethanolamine | HPLC | <1 ppm |
| Residual Blood Group Substance | Immunoprecipitation | Not detectable |

EXAMPLE 2

Production of PHP

All operations for PHP synthesis are carried out at 10° C. First, hemoglobin is derivatized in the beta cleft with pyridoxal-5-phosphate and the polypeptides are modified with polyoxyethylene. Purified stroma free hemoglobin is deoxygenated by bubbling nitrogen through the solution. N-octanol is added to the solution (approximately 0.3 mL per liter of hemoglobin solution) as an antifoaming agent. 16 gm of pyridoxal-5-phosphate are added per kg of hemoglobin present and allowed to react for 30 minutes. 11.8 gm of sodium borohydride are added per kg of hemoglobin and allowed to react for 30 minutes. 11.6 grams of glycine are added per kg of hemoglobin. The pH of the solution is adjusted to 8 with phosphoric acid. Approximately a 10× molar excess of polyoxyethylene (compared to hemoglobin) is added to the solution and allowed to react for 20 minutes.

Next, the pH of the solution is adjusted to 7.5 with 1 N sodium hydroxide and the solution is allowed to stand for an additional 20 minutes. 1.2 grams of sodium borohydride are added per kg of hemoglobin and allowed to react for 20 minutes. The solution is then re-oxygenated by bubbling oxygen through the solution. Particulates are removed from the solution by filtration through a series of filters terminating with a 0.2 μM filter. During this process, chemical inactivation of enveloped viruses occurs.

The chemically modified hemoglobin is concentrated 4-fold to about 100 mg/mL hemoglobin on a Pall-Filtron TFF 100,000 molecular weight cutoff T-screen Omega series membrane. The solution is washed with 10 volumes of purified water to remove residual reactants and to reduce the unmodified hemoglobin content. The washed solution is removed from the membrane and diluted to 80 mg/mL hemoglobin. To assure safety and uniformity of the final product, the pyridoxalated polyoxyethylene hemoglobin (PPHb) solution must be free of contaminants as determined by assaying bioburden, endotoxin, and free POE. The physical state of the product is monitored by assaying the pH and conductivity of the solution and the concentrations of hemoglobin, methemoglobin, and sulfhemoglobin. The consistency of the chemical modification process is determined by analyzing the molecular weight, $P_{50}$, and the polydispersity (DCT) of PPHb. Table 3 lists the specifications for the final bulk non-formulated PHP solution.

TABLE 3

Characteristics of PPHb Solution

| Test | Method | Specification |
|---|---|---|
| pH | pH meter | 8.0 ± 0.5 |
| Conductivity | Conductivity meter | 0.5–2.0 mS/cm |
| Hemoglobin Concentration | CO-Oximeter | 90–120 mg/ml |
| Methemoglobin Content | CO-Oximeter | <7% |
| Sulfhemoglobin Content | Spectrophotometric | <3% |
| $P_{50}$ | Hemox | 15–25 mm Hg |
| Molecular Weight | HPLC | 75k–126k |
| DCT | HPLC | >80% |
| Free POE | Spectrophotometric | <2.2 mg/ml |
| Endotoxin | LAL | <1 EU/ml |

Electrolytes are added to the PPHb solution described above, and the hemoglobin concentration is adjusted to 8% to achieve the final dosage form of PHP. The formulated solution is sterile filtered through a 0.1 μm filter and filled into product containers.

The final product quality is monitored by assessing sterility, general safety, pyrogen content, and phosphatidylethanolamine content. The integrity of hemoglobin is assessed by measuring $P_{50}$, hemoglobin concentration, methemoglobin content, molecular weight and DCT of PHP. The physical state of the product is assessed by measuring pH and osmolality of the final product. The various chemical and physical characteristics of the final PHP product are shown in Tables 4 and 5.

Electrolytes are added to make the solution iso-osmotic compared to blood. A substantially viral free solution comprising pyridoxalated hemoglobin polyoxyethylene (PHP) results. The physical properties and structural characteristics of PHP are described in detail in, for example, U.S. Pat. Nos. 4,301,144, 4,412,989, 4,670,417; Iwashita et al. (1995) *Artificial Red Blood Cell*, John Wiley & Sons; Talarico et al. (2000) *Biochim. Biophys. Acta* 1476:53–65; all of which are herein incorporated by reference.

TABLE 4

Characteristics of Pyridoxalated Hemoglobin Polyoxyethylene Conjugate (PHP)

| Test | Assay Method | Specifications |
|---|---|---|
| Appearance | Visual Inspection | Dark Red Solution |
| pH at 20° C. ± 2° C. | USP | 7.5 ± 0.5 |
| Osmolality (mmol/kg) | Osmometer | 240–300 |
| $P_{50}$ (mm Hg) | HEMOX | 20.0 ± 5.0 |
| Met-Hb (%) | Co-oximeter | <15.0 |
| DCT (%) | HPLC | >80 |
| Molecular Weight (k) | HPLC | 75–126 |
| Total Hb Concentration (mg/mL) | Co-oximeter | 80 ± 8.0 |
| Phosphatidylethanolamine (ppm) | HPLC | <1 |
| Sterility | USP | Sterile |
| General Safety Test | USP | Pass |
| Pyrogen | USP | Pass |
| Endotoxin (EU/mL) | USP (LAL) | <1.0 |

TABLE 5

Additional Characteristics of PHP

| Test Method | Average ± SD |
|---|---|
| Sulfhemoglobin (%) | 0.75 ± 0.27 |
| Free Iron (ppm) | 2.5 ± 0.9 |
| Spectroscopy: UV (nm) | 276.5 ± 1.1 |
| Delta (nm) | 341.5 ± 2.8 |
| Soret (nm) | 414.3 ± 0.4 |
| Beta (nm) | 541.7 ± 0.3 |
| Alpha (nm) | 576.8 ± 0.3 |
| Residual Antifoam (ppm) | 4.0 ± 3.5 |
| Residual Ethanol (ppm) | 2.4 ± 1.1 |
| Surface Antigen A | Negative |
| Surface Antigen B | Negative |

EXAMPLE 4

Reduction of Viral Activity

A. Assays for Virus DNA in Final Product:

The production process was validated for the removal of HIV at one fortieth of a typical production scale. Parameters such as hemoglobin and methemoglobin content, pH, endotoxin content, $P_{50}$, molecular weight, etc. were monitored for the scaled down process to assure that the process parameters at this scale were comparable to the full scale process. Spikes of HIV culture were made into the starting process stream. Starting material, process intermediates, and product were assayed for infectious virus by plaque assay and HIV core protein by ELISA methods, respectively. The plaque assay was performed in duplicate with the MT-4 cell line.

The clearance factor for HIV for the PHP production process described above was shown to be ≧12.85 logs as measured by counting plaque forming units (PFUs).

A study was performed to determine if viral DNA was present in the final product in seven lots of PHP. The absence of viral DNA was detected by DNA hybridization techniques using virus specific probes for hepatitis B virus, cytomegalovirus, herpes simplex virus and epstein-barr virus. DNA was extracted from PHP samples using a phenol based method. Extracted DNA was blotted and probed with $^{32}$P-labeled or biotin labeled DNA specific for the virus. Signals from seven lots of PHP were compared to standards of DNA (100-0.3 pg DNA) contained on the same blot and scored based on the signal intensity. All seven lots of PHP were found to be below the detection limit for the presence of DNA from hepatitis B virus, cytomegalovirus, herpes simplex virus, and epstein-barr virus.

In addition to the virus safety studies summarized above, further virus validation studies for the PHP production process have been conducted. The viruses chosen for these studies included hepatitis A virus (HAV) which is known to be transmitted by blood products, and bovine viral diarrhea (BVD) virus that is a model for hepatitis C virus (HCV) (see Table 6).

The virus validation studies were conducted using scaled down unit operations that accurately represented the process scale operations with respect to physical operating conditions, product intermediates, and final product. The virus cultivation and quantitation was performed in accordance with GLP. Validation of virus quantitation was performed prior to analysis. Reduction levels were derived using sound statistical methods and represent a 95% confidence level.

TABLE 6

Characteristics of Virus Models Used in PHP Process Validation Study

| Model | Family | Genome | Enveloped | Size (nm) | Resistance | Representative Viruses |
|---|---|---|---|---|---|---|
| HIV | Retro | ss-RNA | yes | 80-100 | Low | Human T cell leukemia virus types I & II (HTL V-I & II) Human immunodeficiency virus types 1 & 2 (HIV-1 & 2) |
| BVD | Flavi | ss-RNA | yes | 50-70 | Med | Hepatitis G; Hepatitis C (previously NANBHV), HCV |
| HAV | Picoma | ss-RNA | no | 25-30 | Med-High | Hepatitis A virus, HAV |

Inactivation of Bovine Viral Diarrhea (BVD) Virus in the Final PHP Product

Chemical modification of hemoglobin to produce PHP requires the use of strong reducing agents, alcohol, vitamins, and amino acids. The strong reducing agents and/or alcohols were expected to inactivate enveloped viruses. In order to validate this inactivation, a study was designed to reproduce the chemical modification reaction at one hundredth of a typical full scale reaction. A small reactor was fabricated and equipped with a stirring mechanism, gas distribution manifold, temperature control system and pH meter. The hemoglobin solution was deoxygenated, reacted and reoxygenated under conditions equivalent to those used at production scale. The efficiency of modification was measured by HPLC and physical parameters of the product were determined by assays used by quality control to assess process intermediates. All analysis confirmed that the product of the reaction was equivalent to full scale process product. The starting material was spiked with BVD Virus to a concentration of 10% of the total starting volume before deoxygenation. The reaction was carried out according to the manufacturing protocol and the final product for the unit operation was sampled. The inactivation process eliminated $\geq 5.11\pm0.18$ logs of BVD Virus.

B. Assays for Reduction of Viral Activity by the "First Filtration Means":

Removal of Hepatitis A Virus (HAV) by Ultrafiltration

Purification of hemoglobin from red blood cells is accomplished through a series of filtration steps. As defined herein, the "first filtration means" is an ultrafiltration step that is effective in the removal of virus. In order to validate this, a scaled down (one hundredth of a typical production scale) hollow fiber membrane unit with fiber length identical to the full scale process filters was utilized in a small scale unit operation. Starting material for the validation study was obtained from a full scale manufacturing process stream and represented typical material used in the production of PHP. All process parameters for the operation of the small scale ultrafiltration unit were documented in PHP production batch records. The cross flows, operating pressures, temperature, buffers, and operating times were representative of the full-scale manufacturing process. The only parameter that was modified for the virus validation was the membrane area. Prior to performing the validation study with live virus, several small scale filtration runs were performed to assure that the retentate and permeate streams were equivalent to those obtained from the full scale process.

The input stream was spiked to 1% with HAV and the unit operation was run according to the manufacturing procedure. The titer of HAV in the test samples was determined by performing a $TCID_{50}$ assay with fetal rhesus lung (FrhL-4) cells. The ultrafiltration process eliminated $\geq 5.60\pm0.28$ logs of HAV.

Removal of Bovine Viral Diarrhea (BVD) Virus by Ultrafiltration

Removal of BVD Virus was also validated using the same ultrafiltration membrane unit that was used for the validation of HAV. The process used was similar to the one described above for the HAV validation. The input stream was spiked to 1% with BVD Virus and the unit operation was run according to the manufacturing procedure. The titer of BVD Virus in the test samples was determined by performing a plaque assay with embryonic bovine trachea (EBTr) cells. The ultrafiltration process eliminated $\geq 6.02\pm0.06$ logs of BVD virus.

C. Assays for Reduction of Viral Activity by the "Second Filtration Means":

Removal of Bacteriophage PP7(25 nm)

Sixty ml of purified stroma-free hemoglobin (20 mg/ml) were spiked with 0.5 ml of phage stock (titre=$10^{12}$ PFU/ml). The spiked hemoglobin solution was placed in a stainless steel pressure vessel containing a 47 mm DV-20 filter (Pall). The solution was passed through the DV-20 filter under 30 PSIG. The filtrate was collected and assayed for the presence of PP7 by plaque assay using *Pseudomonas aeurginosa*. The filtration process eliminated 5 logs of PP7. The catalase activity of the hemoglobin solution passed through the filter along with the hemoglobin.

Removal of Bacteriophage PR772 (50 nm)

100 ml of purified stroma free hemoglobin (20 mg/ml) were spiked with 1 ml of Bacteriophage PR772 (titre=4.5× $10^{10}$ PFU/ml). The spiked hemoglobin solution was placed in a stainless steel pressure vessel containing a 47 mm Viresolve NFR filter (Millipore) at the outlet of the vessel. The solution was filtered under pressure at 30 PSIG. The filtrate was collected and assayed for the presence of phage by plaque assay using *Escherichia coli*. The filtration process eliminated $\geq 8$ logs of PR772. The catalase activity passed through the filter along with the hemoglobin.

EXAMPLE 5

Assaying Endogenous Antioxidant Activity

A. PHP molecules synthesized by the methods described above versus hemoglobin molecules and POE-HbA molecules (PHP molecules prepared using a chromatographically purified hemoglobin) were examined with respect to methemoglobin and ferrylhemoglobin formation following $H_2O_2$ challenge (Privalle et al. (1999) *The Biology of Nitric Oxide*, part 7. London: Portland Press, herein incorporated by reference).

Figure 1:
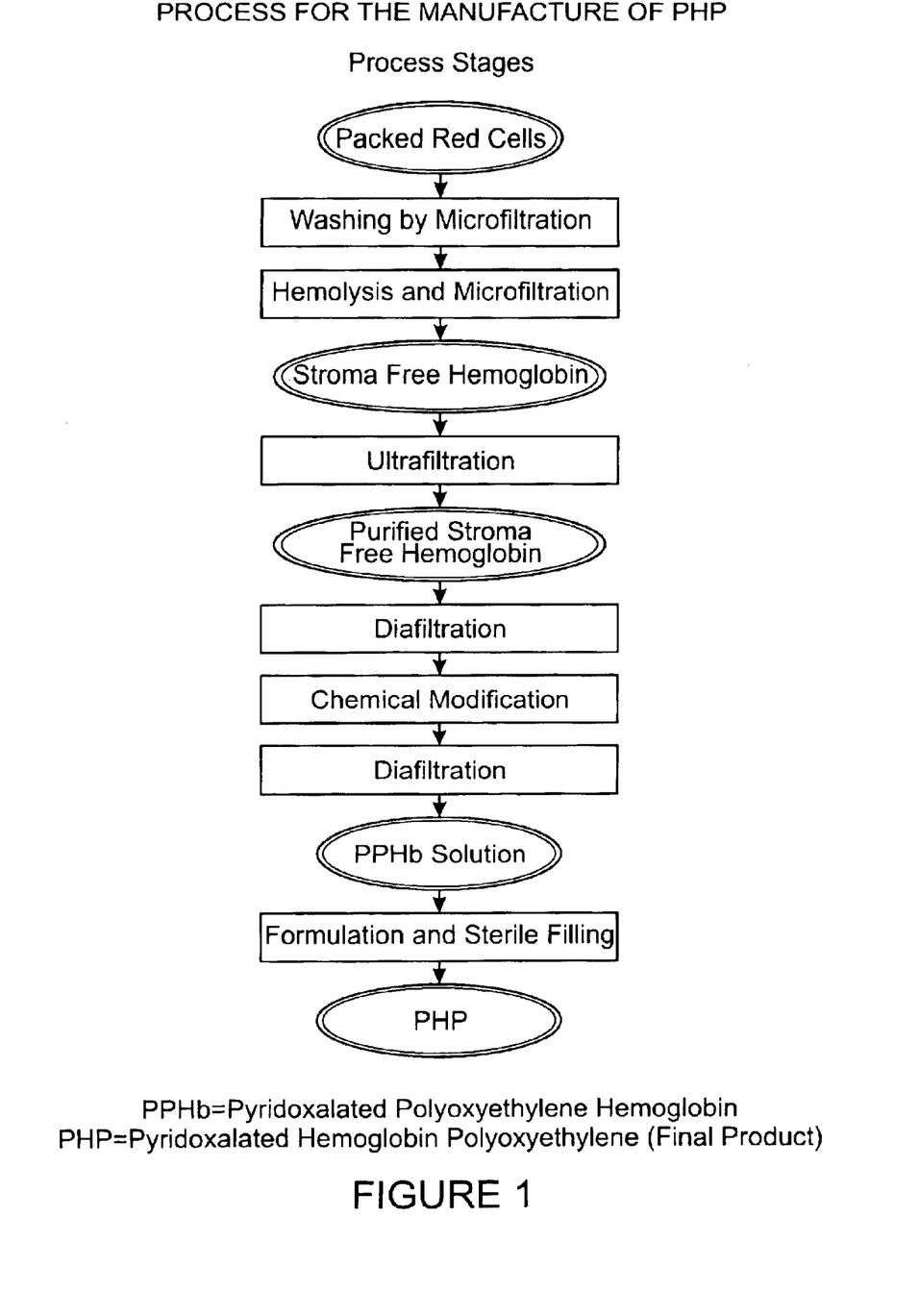
FIG. 1 is a schematic overview of pyridoxalated hemoglobin polyoxyethylene (PHP) synthesis.
Figure 2:
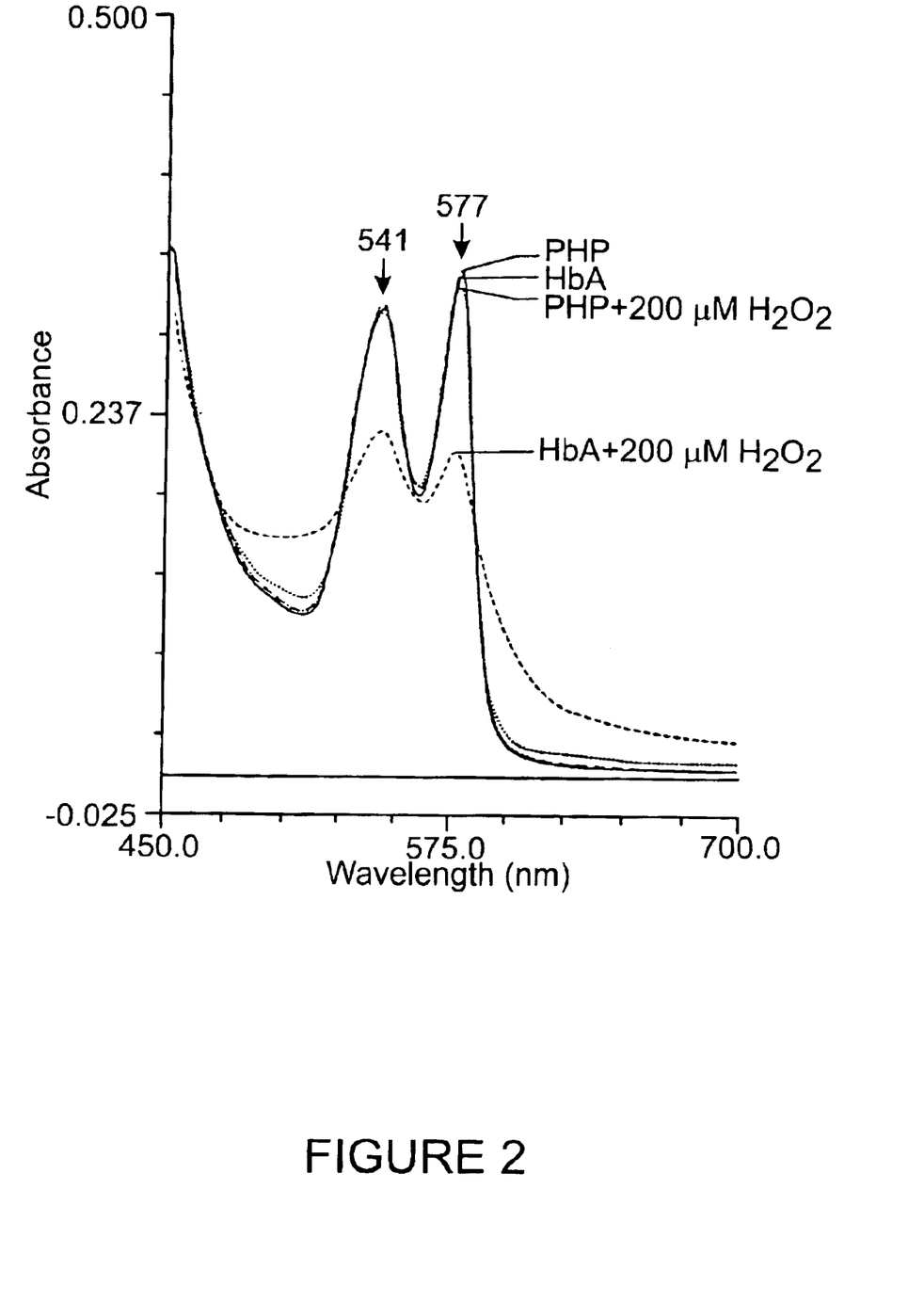
FIG. 2 shows the spectral changes of the hemoglobin molecules of PHP and HbA following oxidation by $H_2O_2$.

Reaction mixtures contained 20 μM (heme) of indicated hemoglobins in 50 μM sodium phosphate, pH 7.4, $H_2O_2$ (200 μM) was added and spectra were obtained after a 5 min incubation at room temperature. Additions of 200 µM $H_2O_2$ to HbA resulted in a decrease in A541 and A577. Quantitation of the hemoglobin oxidation state revealed that approximately 50% of the oxyHbA was converted to metHbA under these conditions. In contrast, PHP was relatively stable to this treatment, with less than 5% of the hemoglobin converted to the methemoglobin form. See FIG. 2.

Figure 3:
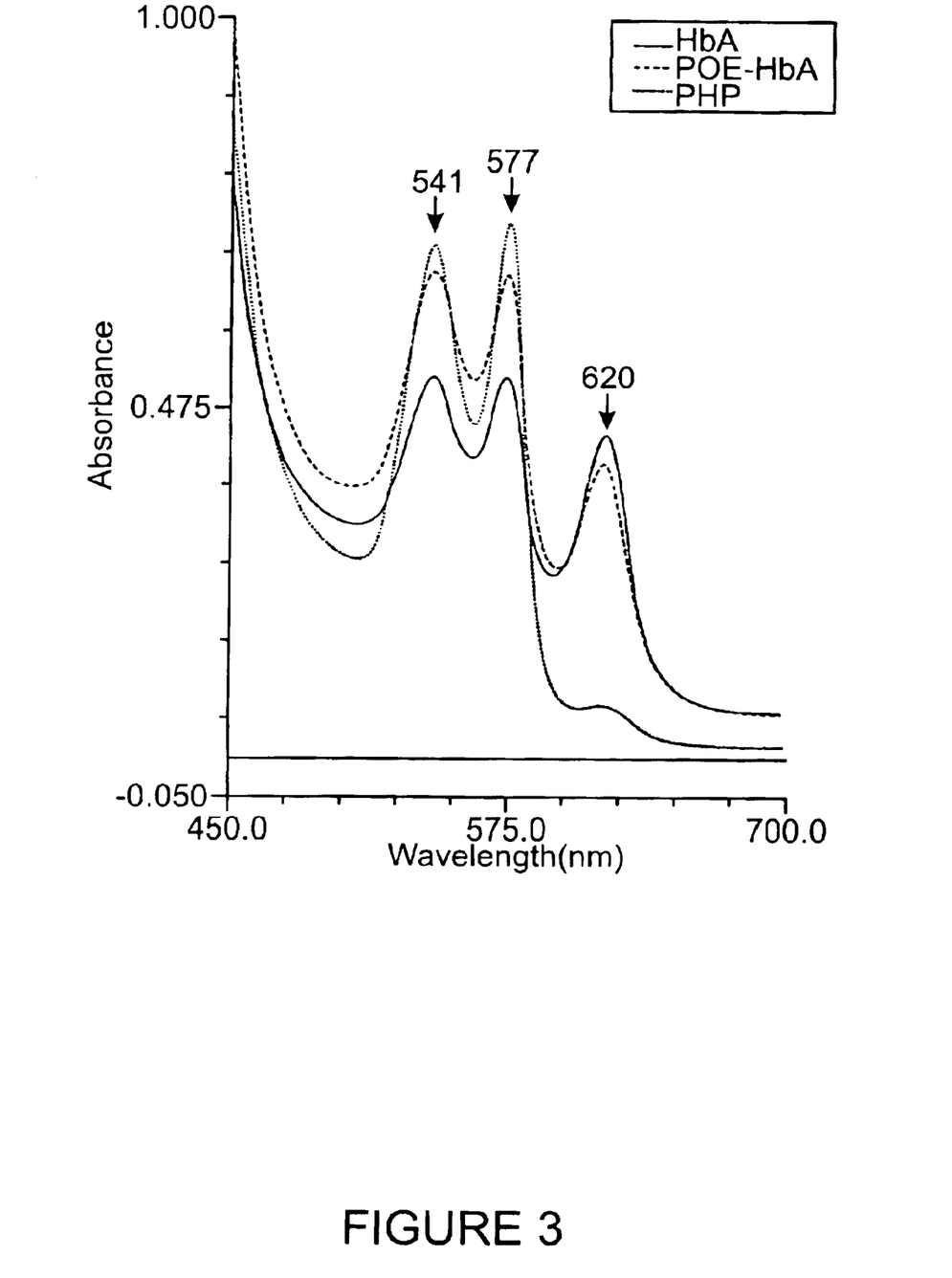
FIG. 3 shows sulfiemoglobin formation ($A_{620}$) following $H_2O_2$-mediated oxidation as a measure of ferrylhemoglobin. The final spectrum for HbA, PHP, and POE-HbA is shown.

The presence of ferrylhemoglobin formation following $H_2O_2$ treatment is shown in FIG. 3. Ferrylhemoglobin can be readily detected spectrophotometrically after addition of $Na_2S$, which results in subsequent formation of sulfhemoglobin. This hemoglobin species is characterized by a distinct peak at 620 nm. The spectrum of the indicated hemoglobin (50 µM heme) was obtained at T=0. A five-fold molar excess of $H_2O_2$ (250 µM) was then added and the reaction mixture incubated for 5 minutes. Catalase (500 units) was added to decompose excess $H_2O_2$. $Na_2S$ (2 mM) was then added and the spectrum obtained after 1 min. The final spectrum for HbA, PHP, and POE-HbA is shown. Following $H_2O_2$ exposure, ferrylhemoglobin formation is much greater in HbA than in PHP.

B. The level of antioxidant activity in units/mg hemoglobin was determined in the final PHP product. Assays to measure antioxidant activity were performed as follows. Table 7 provides the typical antioxidant compositions of PHP.

TABLE 7

Antioxidant Composition of PHP

| Enzyme | Specific Activity |
| --- | --- |
| Catalase | 448 +/− 60 U/mg Hb |
| Glutathione Peroxidase | 120 +/− 24 U/mg Hb |
| Superoxide Dismutase | 1.0 +/− 0.1 U/mg Hb |

The mean catalase activity from red blood cells (RBC), purified stroma free hemoglobin (PSFHb), and PHP, on a hemoglobin basis, is provided in Table 8. The activity is the average catalase activity found over 5 PHP lots.

TABLE 8

| RBC | PSFHb | PHP |
| --- | --- | --- |
| 264 +/− 81 U catalase activity/mg Hb | 239 +/− 19 U catalase activity/mg Hb | 322 +/− 29 U catalase activity/mg Hb |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of preparing a chemically modified hemoglobin solution comprising an endogenous antioxidant enzyme, said method comprising:

a) contacting a stroma free hemoglobin solution with at least one filter, wherein a first filter retains viral particles and allows passage of a filtrate comprising a hemoglobin polypeptide and an endogenous antioxidant enzyme and the filtrate is substantially free of viral contamination;

b) chemically modifying the filtrate with an agent; and, c) isolating the chemically modified hemoglobin solution and the endogenous antioxidant enzyme, wherein at least one of the endogenous antioxidant enzymes retains enzymatic activity.

2. The method of claim 1, wherein at least one of the endogenous antioxidant enzymes retaining enzymatic activity is selected from the group consisting of a superoxide dismutase, a catalase, and a glutathione peroxidase.

3. The method of claim 1, wherein said first filter allows the passage of at least 50% of the endogenous antioxidant enzymes present in the stroma free hemoglobin solution.

4. The method of claim 1, wherein the first filter comprises a 500,000 molecular weight cutoff filter.

5. The method of claim 1, wherein said first filter reduces the passage of viral particles that are between about 200–25 nm in size.

6. The method of claim 1, wherein said first filter reduces the passage of viral particles that are 80–100 nm in size.

7. The method of claim 1, wherein said first filter reduces the passage of viral particles that are between about 80–50 nm in size.

8. The method of claim 1, where said first filter reduces the passage of viral particles that are between about 50–25 nm in size.

9. The method of claim 5, wherein said first filter reduces the passage of said viral particles by about 3 to about 10 log units.

10. The method of claim 1, wherein said first filter produces a filtrate having a viral load reduction of at least 3 log units.

11. The method of claim 1 further comprising contacting the filtrate with a second filter wherein said second filter allows the passage of the hemoglobin polypeptide and the endogenous antioxidant enzyme and retains virus particle.

12. The method of claim 1, wherein the agent is a bifunctional modifying agent.

13. The method of claim 12, wherein said agent is selected from the group consisting of a sebacyl chloride, a glutaraldehyde, a diaspirin derivative, a polyaldehyde, a polyoxyetheylene, a dextran, and an insulin.

14. The method of claim 12, wherein the agent is a bifunctional polyoxyotheyleno.

15. The method of claim 1, wherein the agent is a mixture of a bifunctional and a monofunctional polyoxyethylene.

16. The method of claim 14, wherein the chemically modified hemoglobin solution comprising an endogenous antioxidant enzyme is PHP.

17. The method of claim 1, wherein chemically modifying said filtrate with an agent comprises deoxygenation and pyridoxalation.

18. The method of claim 1, wherein said chemically modified hemoglobin solution comprising an endogenous antioxidant enzyme comprises a hepatitis A viral titer of loss than about 1 $TCID_{50}$ unit/ml.

19. The method of claim 1, wherein the chemically modified hemoglobin solution comprises about a 50% to about a 200% increase in endogenous red blood cell antioxidant activity per unit of hemoglobin found in red blood cells.

20. A method of preparing a chemically modified hemoglobin solution comprising an endogenous antioxidant enzyme, said method consisting of:

a) contacting a stroma free hemoglobin solution with at least one filter, wherein a first filter retains viral particles and allows passage of a filtrate comprising a hemoglobin polypeptide and the endogenous antioxidant enzyme and the filtrate is substantially free of viral contamination;

b) chemically modifying the filtrate with an agent; and, c) isolating the chemically modified hemoglobin solution and the endogenous antioxidant enzyme.

* * * * *

UNITED STATES PATENT AND TRADEMARK OFFICE
CERTIFICATE OF CORRECTION

PATENT NO. : 6,747,132 B2
DATED : June 8, 2004
INVENTOR(S) : Privalle et al.

It is certified that error appears in the above-identified patent and that said Letters Patent is hereby corrected as shown below:

Column 22,
Line 48, "polyoxyetheylene" should read -- polyoxyethylene --;
Line 50, "polyoxyotheyleno" should read -- polyoxyethylene --;
Line 61, "loss" should read -- less --.

Signed and Sealed this

Fourteenth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,747,132 B2
DATED : June 8, 2004
INVENTOR(S) : Privalle et al.

It is certified that error appears in the above-identified patent and that said Letters Patent is hereby corrected as shown below:

Title page,
Item [56], References Cited, U.S. PATENT DOCUMENTS, add
-- 6,054,427 A  4/2000  Winslow   514/6 --.

Signed and Sealed this

First Day of February, 2005

JON W. DUDAS
*Director of the United States Patent and Trademark Office*